United States Patent [19]

Haga

[11] Patent Number: 5,745,236

[45] Date of Patent: Apr. 28, 1998

[54] OPTICAL INSPECTING APPARATUS HAVING A FOCUSING SYSTEM WITH A TELECENTRIC OPTICAL SYSTEM AND AN APERTURE STOP

[75] Inventor: Kazumi Haga, Chofu, Japan

[73] Assignee: New Creation Co., Ltd., Tokyo-to, Japan

[21] Appl. No.: 747,993

[22] Filed: Nov. 12, 1996

Related U.S. Application Data

[63] Continuation of Ser. No. 267,928, Jul. 6, 1994, abandoned.

[30] Foreign Application Priority Data

May 31, 1994 [JP] Japan ................. 6-141118

[51] Int. Cl.6 ............................................. G01N 21/00
[52] U.S. Cl. ........................................ 356/371; 356/237
[58] Field of Search ........................... 356/371, 394, 356/445, 446, 121, 237, 375, 376, 129

[56] References Cited

U.S. PATENT DOCUMENTS

| | | |
|---|---|---|
| 3,484,150 | 12/1969 | Taoka et al. ................. 356/371 |
| 3,782,827 | 1/1974 | Nisenson et al. ............. 356/237 |
| 3,815,998 | 6/1974 | Tietze ........................ 356/371 |
| 4,547,073 | 10/1985 | Kugimiya .................... 356/371 |
| 5,048,967 | 9/1991 | Suzuki et al. ............... 356/237 |
| 5,155,558 | 10/1992 | Tannenbaum et al. ........ 356/446 |
| 5,268,735 | 12/1993 | Hayashi ...................... 356/239 |
| 5,311,599 | 5/1994 | Freischlad ................... 356/376 |
| 5,461,228 | 10/1995 | Kirkman et al. ............. 250/223 B |
| 5,497,234 | 3/1996 | Haga .......................... 356/237 |

*Primary Examiner*—Hoa Q. Pham
*Attorney, Agent, or Firm*—Evenson, McKeown, Edwards & Lenahan, P.L.L.C.

[57] ABSTRACT

An optical inspecting apparatus illuminates a sample with at least one of a parallel light or a diffused light. Light reflected from the sample or light transmitted through the sample is focused by a telecentric optical system and an aperture stop arranged at a back focal plane in the image space of the telecentric optical system. The sample is viewed based on light thus obtained.

12 Claims, 7 Drawing Sheets

OPTICAL INSPECTING APPARATUS HAVING A FOCUSING SYSTEM WITH A TELECENTRIC OPTICAL SYSTEM AND AN APERTURE STOP

This application is a continuation of application Ser. No. 08/267,928, filed on Jul. 6, 1994 now abandoned.

BACKGROUND OF THE INVENTION

1. Field of the Invention

This invention relates to an optical inspecting apparatus for two-dimensionally viewing a surface of a sample or the like, and more particularly to an optical inspecting apparatus of this kind which is suitable, e.g. for inspecting the state or condition of a surface (hereinafter referred to as a "sample surface") of a sample, such as a mirror-finished surface wafer, or for detecting a symbol, particularly an ID (identification) number (serial number as an identifier), formed on the sample surface.

2. Prior Art

Conventionally, an optical inspecting apparatus is used for detecting an ID number formed on a sample surface of a member used for manufacturing semiconductor integrated circuits, or for checking the state of the sample surface, for an undulation, a dimple, a projection, insufficient wash, or buff damage, etc. As such a conventional inspecting system, a type is known in which halogen light converted into a point source of light is transmitted to a half mirror, and light reflected therefrom is converted by a collimator lens into a parallel light for illuminating a sample surface in a normal direction or perpendicular to the sample surface. The light reflected from the sample surface is caused to be transmitted through a collimator lens, again, into a schlieren optical system, to be focused, thereby performing inspection of the state of the sample surface.

The schlieren optical system used in the inspecting apparatus is one of typical optical systems for indicating variations in refractive index, reflectance, and transmittance resulting from the irregularities on the sample surface or the internal condition of the sample, as differences in brightness. This optical system is adapted to cause the light reflected from the sample surface to be focused by the collimator lens, and a knife edge arranged on a back focal plane in an image space thereof intercepts part of the light scattered from the sample surface, thereby permitting a reflected image of the sample surface or the like to be viewed at a viewing block by the eye or by the use of a camera or other devices.

According to this optical system, if there are irregularities on the sample surface, the light is scattered from these irregularities. Part of the scattered light from the irregularities hits against the knife edge, and is prevented from reaching the viewing block. As a result, when viewed frog behind the knife edge, a portion of the sample surface corresponding to the scattered light intercepted by the knife edge becomes darker than the rest the sample surface. The pattern of bright and dark portions corresponds to the state of the sample surface, which enables the state of the sample surface to be judged therefrom.

However, the conventional optical inspecting apparatus suffers from the following problems:

In the inspecting system utilizing the schlieren optical system, the collimator lens for focusing the light reflected from the sample surface is positioned close to the sample surface, and hence the depth of field is narrow, so that if there is a large curvature or undulation on the sample surface, a portion thereof to be observed does not properly fall within a range in which a focused image can be obtained. This also applies to the case in which the sample is observed by light transmitted therethrough. Therefore, an optical inspecting system has been desired, which provides a wide focussable range in which an object to be viewed can be focused.

With an illuminating optical system as well, the conventional apparatus necessitates a reflector for converting the halogen light into a point source of light and a pinhole arranged at a focal point of the reflector, a wavelength-selecting filter for restricting the wavelength of an illuminating light, a diffuser for diffusing the halogen light to thereby cancel a light source image, and a polarized light filter for restricting the transmission of the scattered light. Therefore, the reduction of the number of component parts has been desired to reduce the manufacturing costs.

SUMMARY OF THE INVENTION

It is a first object of the invention to provide an optical inspecting apparatus which is capable of increasing the depth of field to provide a wide focussable range for an object of inspection.

It is a second object of the invention to provide an optical inspecting apparatus which is capable of being manufactured at reduced manufacturing costs.

To attain the above objects, according to a first aspect of the invention, there is provided an optical inspecting apparatus including:

illuminating means for illuminating a sample with an illuminating light;

focusing means for focusing a reflected light reflected from the sample or a transmitted light having transmitted through the sample;

viewing means for presenting an image of the sample based on a light transmitted through the focusing means.

The optical inspecting apparatus according to the first aspect of the invention is characterized in that the focusing means comprises a telecentric optical system and a aperture stop arranged on a back focal plane or in its vicinity of the telecentric optical system in an image space thereof.

According to the optical inspecting apparatus of the first aspect of the invention, when the object is illuminated by the parallel light, the reflected light reflected from the sample or the transmitted light transmitted through the sample is focused by the telecentric optical system, and the transmitted via the aperture stop arranged on a back focal plane or in its vicinity of the telecentric system in an image space thereof to enter the viewing block. As a result, a viewer (a person who views) can view an image formed within the viewing block. Further, the distance (object space distance) between a lens as part of the telecentric optical system and the sample surface can be set as desired, and hence by increasing the distance, the depth of field can be increased. Therefore, even if there is a large undulation on the sample surface, the whole of the object of inspection is focussable. Further, sensitivity of the apparatus can be adjusted by adjustment of the aperture stop, which makes it possible to markedly improve the definition of the pattern of brightness and darkness corresponding to a two-dimensional status of part of the sample surface to be checked.

In one preferable embodiment, the illuminating means includes parallel light-forming means for forming a parallel light to illuminate the sample therewith.

According to this preferred embodiment, by illuminating a flat part of the sample surface in a normal direction, for example, with the parallel light, it is possible to detect the flat part from which the parallel light is reflected normally as a bright portion area, and irregularities on the surface from which the parallel light is irregularly reflected as dark portions. Therefore, it is possible to detect the state of the sample surface as a pattern of bright portions and dark portions of the image. Further, since the parallel light is used for illumination, in cases where light reflected from the portion to be viewed travels in an uniform direction, e.g. when the portion is formed by grooves having a V-shaped cross-section (hereinafter referred to as "the V-shaped grooves"), a portion to be viewed can be clearly viewed, by viewing the uniformly reflected light alone.

In another preferable embodiment, the illuminating means includes diffused light-forming means for forming a parallel light to illuminate the sample therewith.

According to this preferred embodiment, since the sample is illuminated with the diffused light, light is reflected from a portion to be observed in various directions. Therefore, when the portion is in the form of recesses, it is possible to clearly view the portion by detecting a portion of light reflected from the recesses in a normal direction or a direction perpendicular to the plane of the sample surface, since none of the diffused light cast on the flat surface of the sample is reflected therefrom toward the focusing means positioned in a normal direction or perpendicular to the plane of the sample surface.

In still another preferable embodiment. the illuminating means includes parallel light-forming means for forming a parallel light to illuminate the sample therewith and diffused light-forming means forming a diffused light to illuminate the sample therewith.

According to this preferred embodiment, it is possible to adjust a mixing ratio of the parallel light and the diffused light to meet the kind of a portion to be viewed, to thereby clearly view the portion.

Preferably, the focusing means includes inclination-adjusting means for inclining an optical axis thereof with respect to a light path of the reflected light or the transmitted light.

According to this preferred embodiment, the optical axis of the focusing means can be inclined with respect to the light path of the reflected light or the transmitted light. Therefore, by setting the inclination of the focusing means such that a portion of light reflected from V-shaped grooves, convexes/concaves or the like of the sample surface travels in a predetermined direction to enter and pass through the telecentric optical system, and at the same time light reflected from the sample surface in a normal direction does not enter the telecentric optical system, it is possible to invert the pattern of bright portions and dark portions of the image corresponding to the V-shaped grooves, irregularities, or the like of the sample surface, which can provide a pattern easier to be viewed depending on the nature of the sample.

Preferably, the illuminating means comprises an LED for generating a diffused bundle of rays, as a light source.

According to this preferred embodiment, since the light source is formed by the LED for generating a diffused bundle of rays, the apparatus dispenses with a reflector, a wavelength-selecting filter, a diffuser, a polarized filter, and other devices, including ones required in converting light emitted from a light source having directivity, such as a lamp, into a point source of light, which contributes to reduction of manufacturing costs.

Preferably, the viewing means has a light receiving block for receiving the light passed through the focusing means, and for generating and delivering an image signal, and an image processing block for performing image processing based on the image signal delivered from the light receiving block.

According to this preferred embodiment, since the optical inspecting system further comprises the light receiving block and the image processing block for performing image processing based on the image signal delivered from the light receiving block, it is possible to obtain a clear image of the object.

Further preferably, the optical inspecting apparatus further comprises light level adjusting signal-generating block for generating a light level control signal for setting a white level voltage or a black level voltage of the image signal to a predetermined value, and a light level control block for changing the light level of the parallel light, based on the light level control signal.

According to this preferred embodiment, when the light level control signal-generating block delivers the light level control signal to the light level control block, which in turn changes the light level of the parallel light such that the white level voltage or the black level voltage of the image signal becomes equal to a predetermined value, whereby the level of the image signal generated based on the parallel light is prevented from being saturated, which makes it possible to view the object illuminated in a proper light level.

Also preferably, the optical inspecting apparatus further comprises light level adjusting signal-generating block for generating a light level control signal for setting a white level voltage or a black level voltage of the image signal to a predetermined value, and a light level control block for changing the light level of the diffused light, based on the light level control signal.

According to this preferred embodiment, when the light level control signal-generating block delivers the light level control signal to the light level control block, which in turn changes the light level of the diffused light such that the white level voltage or the black level voltage of the image signal becomes equal to a predetermined value, whereby the level of the image signal generated based on the diffused light is prevented from being saturated, which makes it possible to view the object illuminated in a proper light level.

Also preferably, the optical inspecting apparatus further comprises light level adjusting signal-generating block for generating a light level control signal for setting a white level voltage or a black level voltage of the image signal to a predetermined value, and a light level control block for changing the light level of the parallel light and the light level of the diffused light independently of each other, based on the light level control signal.

According to this preferred embodiment, when the light level control signal-generating block delivers the light level control signal to the light level control block, which in turn changes the light level of the parallel light and the light level of the diffused light independently of each other such that the white level voltage or the black level voltage of the image signal becomes equal to a predetermined value, whereby the level of the image signal generated based on the parallel light and the diffused light is prevented from being saturated, which makes it possible to view the object illuminated in a proper light level.

According to a second aspect of the invention, there is provided an optical inspecting system comprising:

illuminating means for illuminating a sample having an ID number-formed portion in which an ID number is formed in the form of grooves or in the form of dots, with at least one of a parallel light and a diffused light;

focusing means for focusing a reflected light reflected from the ID number-formed portion of the sample or a transmitted light transmitted through the ID number-formed portion of the sample, the focusing means comprising a telecentric optical system and a aperture stop arranged on a back focal plane or in its vicinity of the telecentric optical system in an image space thereof; and viewing means for presenting an image of the sample based on a light passed through the focusing means.

According to the optical inspecting system of the second aspect of the invention, by illuminating the ID number as the object to be viewed with at least one of the parallel light and the diffused light depending on the type of the ID number, which may be formed as grooves, or in dots, it is possible to more clearly view the ID number.

According to a third aspect of the invention, there is provided an optical inspecting system comprising:

illuminating means for illuminating a sample having an ID number-formed portion in which an ID number is formed in the form of V-shaped grooves or in the form of dots, with at least one of a parallel light and a diffused light;

focusing means for focusing a reflected light reflected from the ID number-formed portion of the sample or a transmitted light transmitted through the ID number-formed portion of the sample, a light receiving block for receiving a light passed through the focusing means, and for generating and delivering a image signal;

an image processing block for performing image processing based on the image signal delivered from the light receiving block;

light level adjusting signal-generating block for generating a light level control signal for setting a white level voltage or a black level voltage of the image signal to a predetermined value; and a light level control block for changing at least one of the light level of the parallel light and the light level of the diffused light independently of each other, based on the light level control signal.

According to the optical inspecting apparatus of the third aspect of the invention, it is possible to more clearly view the ID number by the operation of the optical inspecting apparatus, which is described in the first aspect of the invention.

The above and other objects, features, and advantages of the invention will become more apparent from the following detailed description taken in conjunction of the accompanying drawings.

DETAILED DESCRIPTION

Next, the invention will be described in detail with reference to drawings showing a preferred embodiment thereof.

Figure 1:
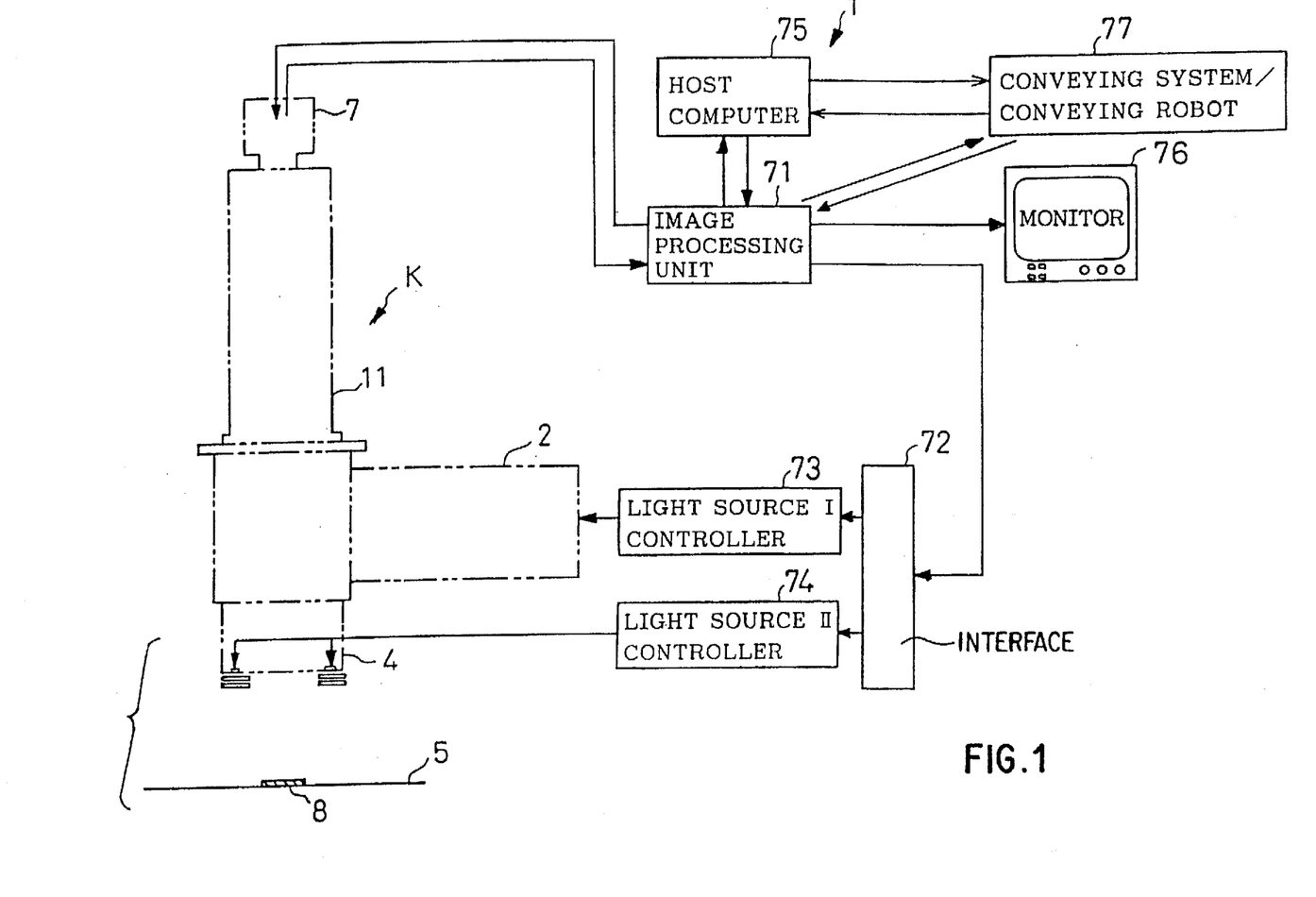
FIG. 1 is a block diagram schematically showing the whole arrangement of an optical inspecting apparatus according to an embodiment of the invention.
Figure 2:
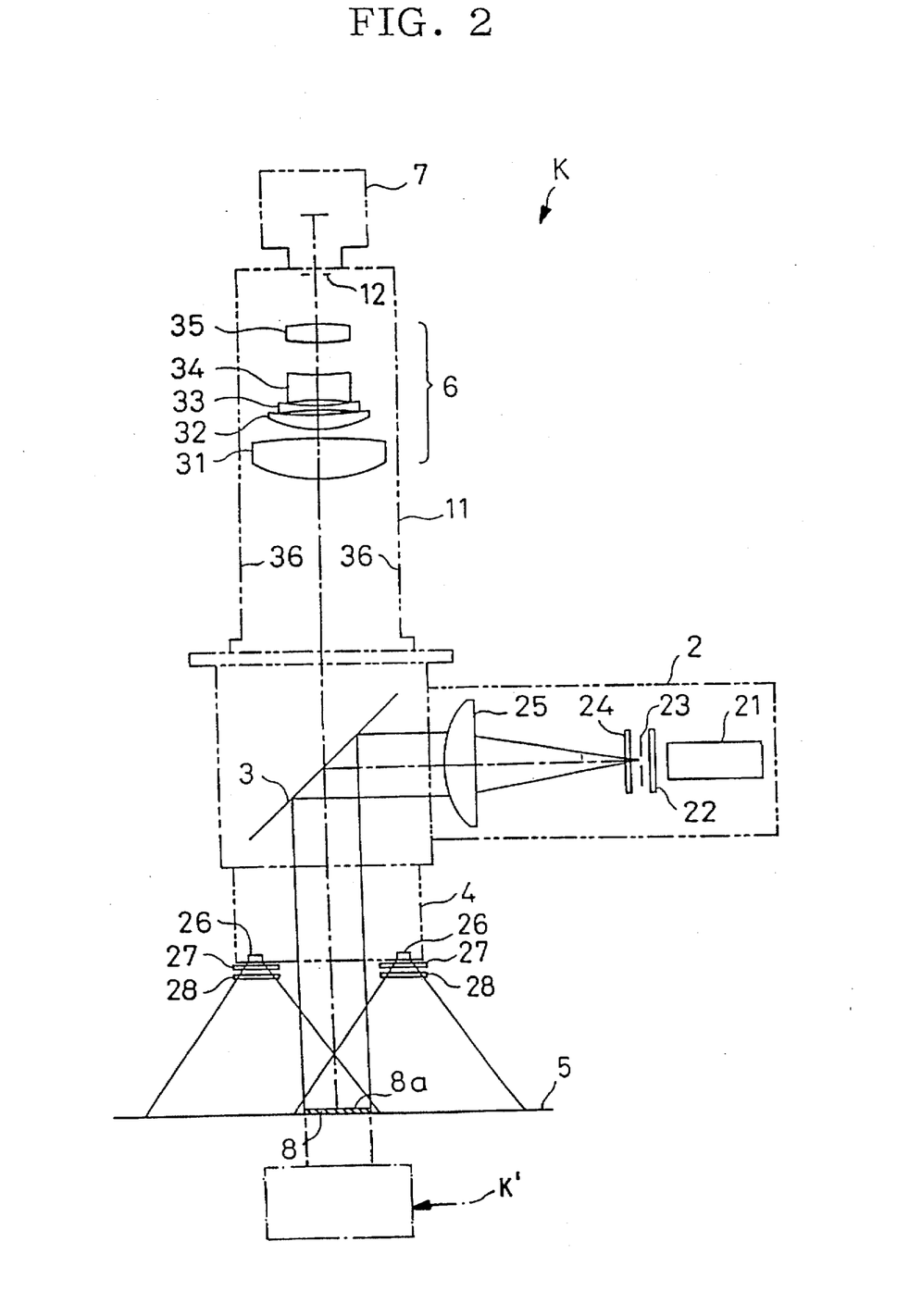
FIGS. 2 and 2A are diagrams showing the construction of an optical system of the optical inspecting apparatus according to preferred embodiment.

Referring first to FIG. 1, reference numeral 1 generally designates an optical inspecting apparatus according to the invention. The optical inspecting apparatus of the invention is mainly comprised of an optical system K, an image processing unit 71, an interface 72, a light source I controller 73, a light source II controller 74, a host computer 75, a monitor 76, and a conveying system/conveying robot 7. As shown in FIG. 2, the optical system K is comprised of a light source block 2, a half mirror 3, an auxiliary light source block 4, a tilting stage 5, a telecentric optical system 6, and a viewing block 7. The telecentric optical system 6 is supported by a lens barrel 11.

Now, the optical inspecting apparatus will be described in more detail. The optical system K illuminates a sample 8, such as a semiconductor wafer, with a parallel light and/or a diffused light, and utilizes light reflected from a sample surface 8a to check for irregularities of the sample surface 8a or an ID number formed thereon. The image processing unit 71 amplifies an image signal delivered from a CCD (charge-coupled device) arranged within the viewing block 7, and then delivers the resulting signal as a video signal to the monitor 7, or further converts same into a digital signal to deliver same as a digital image signal to the host computer 75. The image processing unit 71 also delivers a light level control signal to the light source I controller 73 and the light source II controller 74 such that the white level voltage (voltage of the image signal at which the maximum brightness of an image is reached) falls within a predetermined range, i.e. for prevention of saturation of the white level voltage, to thereby control the level of lights emitted from the light source blocks within the optical system. More specifically, the image processing unit 71 delivers, via a RS-232C line, the light level control signal formed in 8-bit serial data to the interface 72, which converts the serial data into a parallel data signal having eight bits and delivers the resulting parallel data signal to both the light source I controller 73 and the light source II controller 74. These controllers 73, 74 control the levels of lights emitted from the light source block 2 and the auxiliary light source block 4.

The host computer 75 recognizes an ID number formed on the sample surface 8a based on the digital image signal delivered from the image processing unit 71, and based on the ID number thus detected, performs check on the steps of manufacturing semiconductor wafers, and various kinds of statistical processing. Further, the host computer 75, upon recognition of the ID number of the sample, starts to perform control to drive the conveying system/conveying robot 77 for conveying a subsequent sample 8 to the tilting stage 5.

The optical inspecting apparatus may be constructed such that the conveying system/conveying robot 77 is directly controlled by the image processing unit 71.

Next, an outline of operations of the optical system K will be described with reference to FIG. 2. The illuminating light emitted from the light source block 2 is reflected by the half mirror 3, thereby illuminating the sample surface 8a of the sample 8 placed on the tilting stage 5 in a normal direction, i.e. in a direction perpendicular to the sample surface 8a. The resulting light reflected from the sample surface 8a is transmitted in a direction opposite to that of the illuminating light to pass through the half mirror 3, and then focused by the telecentric optical system 6, described in detail hereinafter, arranged within the lens barrel 11. The focused light is permitted to pass through an aperture stop 12 to be detected as an image at the viewing block 7. Since it is not required to interpose lens for focusing the reflected light between the sample surface 8a and the telecentric optical system 6, it is possible to increase the distance between a lens of the telecentric optical system and the sample, thereby enabling the depth of field to be increased. As a result, a focussable range of the object is increased, which makes it easier to position the whole of a portion to be viewed within the focussable range, even if there is a large curvature or undulation on the sample surface 8a.

Further, in the event that minute irregularities additionally formed on the sample surface 8a having such a large undulation, it is possible to adjust the sensitivity of the apparatus by adjusting the aperture stop 12 or by inclining the lens barrel 11 by means of an inclining mechanism provided therefor, described hereinafter. More specifically, there are cases where a coating, such as an aluminum coating, a passivation coating, or a photoresist coating, is provided, covering ID numbers (portions to be viewed) formed in V-shaped grooves, ID numbers (portions to be viewed) formed in a plurality of dots, or the like. In order to view these ID numbers alone instead of viewing such a coating, the lens barrel 11 is inclined by the inclining mechanism, to prevent the white level voltage or the black level voltage from being saturated, and the aperture stop 12 is narrowed such that only light reflected from a portion (ID number-formed portion) of the sample at which the ID number is formed, is permitted to pass through the aperture stop 12, thereby enabling irregularly reflected components of light from the sample surface 8a to be shut off. This makes it possible to view a clear image of the ID number of the sample 8 by the viewing block 7. The pattern of bright portions and dark portions of the image thus produced reflect the state of the sample surface 8a, such as irregularities and the ID number formed thereon. Therefore, by viewing the image output from the viewing block 7, it is possible to view or observe a two-dimensional distribution of minute changes in the sate of the sample surface 8a.

Next, the optical inspecting system 1 of the present invention will be described in detail.

Referring to FIG. 2, the light source block 2 is comprised of a spot fiber light guide 21, a diffuser 22, an aperture 23, a wavelength-selecting filter 24, and a collimator lens 25. The spot fiber light guide 21 collects light emitted from a halogen lamp, not shown, which operates with an electric power of 100 W or 150 W and is controlled by the light source I controller 73 in respect of the level of the light emitted therefrom, and emits a halogen light from a front open end thereof.

The light emitted from the spot fiber light guide 21 is diffused by the diffuser 22, and then set by the aperture 23 in respect of its illuminance and angle of illumination. Then, the wavelength-selecting filter 24 restricts the light to one having a selected wavelength range, and the collimator lens converts the resulting light into a parallel light, which is transmitted to the half mirror 3. In this connection, the aperture 23 has a function of converting the light emitted from the spot fiber light guide 21 into a point source of light. The wavelength-selecting filter 24 is in the form of a turret equipped with a various types of interference filters, making it possible to properly change the wavelength of an illuminating light for illuminating the sample surface 8a. The wavelength-selecting filter is also used in adjusting the sensitivity of the telecentric optical system 6 of the optical inspecting apparatus 1. For example, when a peak-to-valley value related to irregularities on the sample surface 8a is small, a range of a shorter wavelength is selected.

The half mirror 3 is inclined through 45° with respect to an optical axis of the telecentric optical system 6, and is adapted to reflect the light transmitted from the light source block 2 to cast same on the tilting stage 5, while permitting the light reflected from the sample surface 8a to pass therethrough to reach the telecentric optical system 6.

The auxiliary light source block 4 has a body in the form of a hollow cylinder. On an annular bottom face of the body, there are provided a ring fiber light guide 26, a diffuser 27, and a wavelength-selecting filter 28, each formed in the form of a donut, and mounted on the annular bottom face in the mentioned order. The ring fiber light guide 26 provides a light source auxiliary to that of the light source block 2, and emits halogen light collected from a halogen lamp, not shown, which is controlled in respect of the light level, by the light source II controller 74, toward the tilting stage 5. This light is diffused by the diffuser 27, and then restricted as to its wavelength by the wavelength-selecting filter 28, thereafter illuminating the sample surface 8a of the sample 9 placed on the tilting stage 5. This light serves to improve the contrast of bright portions and dark portions forming a pattern of the image corresponding to the state or condition of the sample surface 8a.

The tilting stage 5 is constructed such that it is capable of finely adjusting the inclination of the sample 8 so as to permit the parallel light as the illuminating light to illuminate the sample surface 8a in a direction perpendicular thereto.

Figure 3:
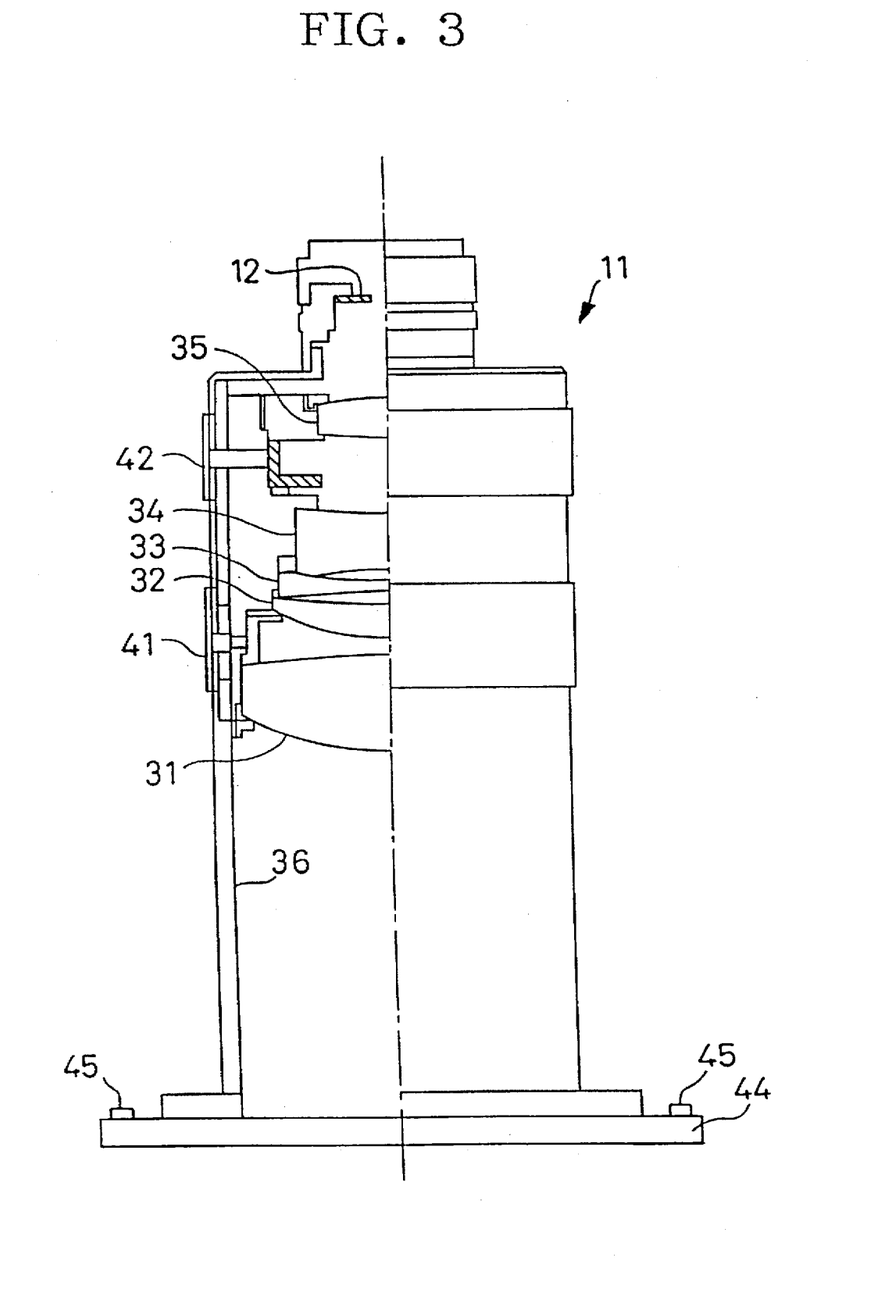
FIG. 3 is a diagram showing an outline of a telecentric optical system for forming a reduced image.
Figure 4:
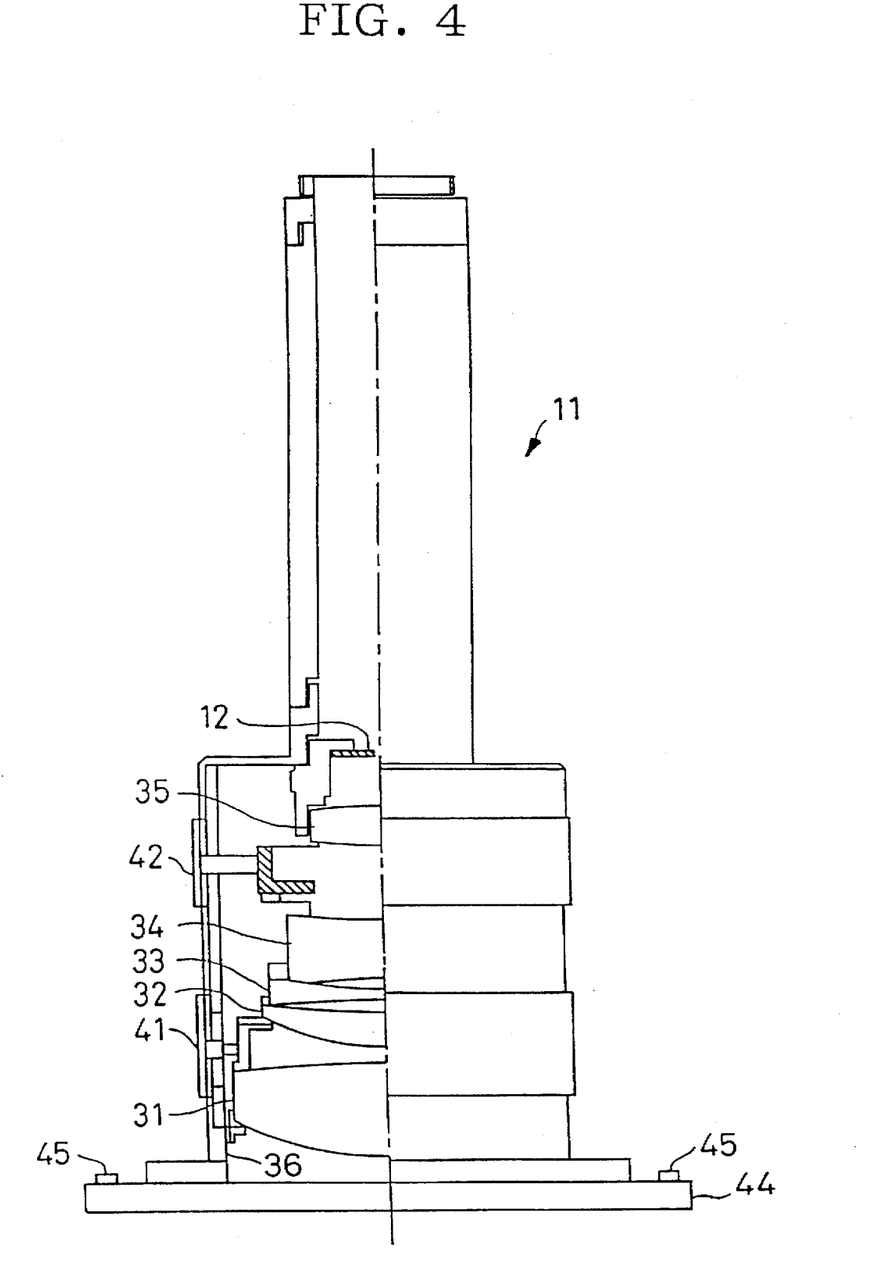
FIG. 4 is a diagram showing an outline of a telecentric optical system for forming an enlarged image.

The lens barrel 11 has an inner wall thereof provided with a shield 36 (or absorber) for prevention of influence of scattered light having large scattering angles, and encloses a telecentric optical system 6 formed of five lenses 31 to 35, with a aperture stop 12 continuously variable in the diameter of a circular opening thereof provided therein. The telecentric optical system 6 is constructed such that the system as a whole has a focal distance of 66 mm, an F number of 4 (which may be variable), and a magnification of 0.32. The whole lens barrel 11 is formed as a replaceable unit for adjustment of the size of an image formed at the viewing block 7. FIG. 3 and FIG. 4 show a lens barrel 11 for use in forming a reduced image, and one for use in forming a magnified image, respectively. As the distance between the sample surface 8a and the lenses 31 is larger, the shield or absorber 36 of the lens barrel 11 has a larger effect of shielding the telecentric system from scattered lights. Further, the lens barrel 11 may be provided with a lens system-moving mechanism in which a unit of lenses 31 to 35 and the aperture stop 12 can be moved toward or away from the viewing block 7, thereby enabling one lens barrel to continuously vary the size of an image formed, between the size of most reduced one and that of the most magnified one.

Further, the lens barrel 11 is provided with a focusing mechanism 41 for adjustment of the distance between the sample surface 8a and the lens 31, which is used in fine adjustment of focusing of the image. Further, a diaphragm 42 for adjusting a diaphragm stop is separately provided in addition to the aperture stop 12, which makes it possible to change the brightness of the image.

The lens barrel 11 is equipped with the aforementioned inclining mechanism for inclining itself with respect to an optical axis of light reflected from the sample surface 8a in a normal direction or direction perpendicular to the sample surface 8a. The inclining mechanism is not particularly limited, but may be formed by three leveling screws 45, 45, 45. It is possible to invert a pattern of bright portions and dark portions by finely adjusting these screws 45 to vary the inclination of the lens barrel 11. The inclining mechanism may be adapted to change the inclination of the half mirror 3, the optical axis of light emitted from the light source block 2, and the inclination of the tilting stage 5. However, in a case where ID numbers formed on samples 8 passing in a manufacturing line are viewed, the tilting stage cannot be employed, and hence it is preferred that the inclination of the lens barrel 11 is varied.

The stop aperture 12 of the lens barrel 11 is an iris diaphragm formed of ten blades, which is adapted to have its diameter of a circular opening thereof continuously changed by a movable adjuster, not shown. The diameter of the circular opening is varied to adjust the sensitivity of the apparatus. The aperture stop 12 is arranged on a back focal plane in an image space of the telecentric optical system 6. When the lens system-moving mechanism is provided, the apparatus is constructed such that the aperture stop 12 is moved to the back focal plane in the image space according to a shift of position of the lens 31 to 35.

The viewing block 7 is not particularly limited, but formed of a CCD (charge-coupled device) having 512×512 picture elements for displaying a two-dimensional pattern of bright portions and dark portions corresponding to the state of the sample surface 8a. An image signal is delivered from the CCD to the image processing unit 71 via a coaxial cable.

Next, operations of the optical inspecting apparatus according to the embodiment will be described.

A portion of the light emitted from the spot fiber light guide 21, which is diffused by the diffuser 22 and then transmitted through the aperture 23 and the wavelength-selecting filter 24, is converted by the collimator lens 25 into a parallel light, which is transmitted to the half mirror 3. The parallel light reflected from the half mirror 3 illuminates the sample surface 8a and is reflected therefrom toward the half mirror 3. In this case, light emitted from the ring fiber light guide 26 also illuminates the sample surface 8a and is reflected therefrom, thereby improving the contrast of a pattern of bright portions and dark portions of the image corresponding to the state of the sample surface 8a.

The reflected light transmits through the half mirror 3 into the lens barrel 11 to form an image on an image-forming plane, i.e. on the CCD of the viewing block 7, located behind the back focal plane of the telecentric optical system in its image space. In this case, the reflected light from irregularities on the sample surface 8a is intercepted or absorbed by the shield 36 of the lens barrel 11, whereas the light reflected from a flat portion of the sample surface 8a is focused by the telecentric optical system 11 to pass through the aperture stop 12 as it is. As a result, portions of the sample surface 8a having irregularities form a dark pattern low in brightness of the formed image, while flat portions of same form a bright pattern high in brightness of same. Furthermore, each portion of the reflected light which is projected on a corresponding portion of the pattern of bright portions and dark portions corresponds to each location on the sample surface 8a in a one-to-one correspondence. Therefore, the pattern of brightness and darkness projected on the CCD reflects minute changes on the sample surface, i.e. irregularities, such as convexes and concaves, formed thereon, so that the image output from the viewing block 7 makes it possible to accurately observe a two-dimensional distribution of minute changes on the state of the sample surface 8a in a real time.

In this case, the adjustment of the focusing mechanism 41 makes it possible to adjust focusing position of the viewing block 7, while the adjustment of the opening of the aperture stop 12 makes it possible to perform a fine adjustment of focusing. Further, the distance between the telecentric optical system 6 and the sample surface 8a can be changed as well to move the viewing block 7 to a height suitable for a person who views to view the image, without making the image obscure or changing the size of the pattern of bright and dark portions, and magnification, since the aperture stop 12 is arranged on the back focal plane of the telecentric optical system 6 in its image space, and at the same time the distance between the telecentric optical system 6 and the viewing block 7 remains fixed.

Further, the fine adjustment of the leveling screws 45 makes it possible to invert the pattern in respect of the bright portions and dark portions. More specifically, when the leveling screws 45 are adjusted to set the inclination of the lens barrel 11 such that the optical axis is made parallel to light reflected from irregularities on the sample surface 8a in a scattered manner, the scattered light passes through the aperture stop 12 as it is, whereas most of the light reflected in a normal or perpendicular direction from flat portions on the sample surface 8a is intercepted by the shield 36 and the aperture stop 12, whereby the irregularities on the sample surface 8a are represented by bright portions while the flat portions on same by dark portions. This contributes to an improved observability of an object to be checked, particularly when the object is formed in the shapes of grooves on the sample surface 8a, and hence light reflected from the grooves tends to travel in fixed directions, as is the case with ID numbers.

Figure 5:
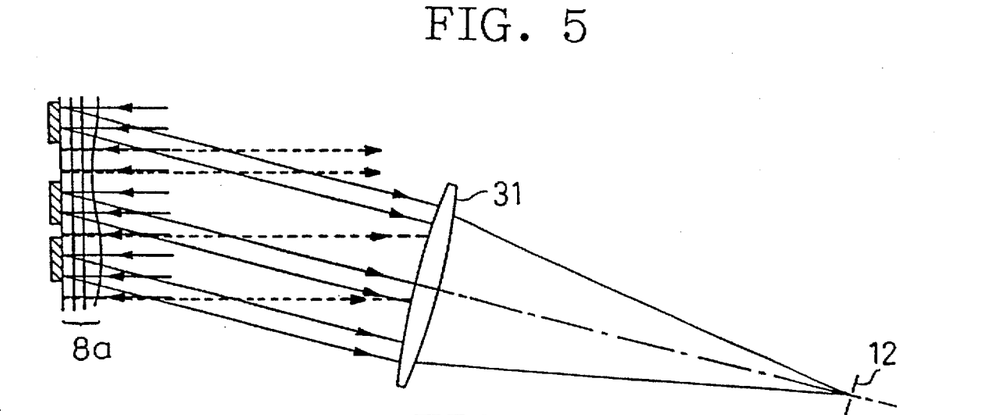
FIG. 5 is a diagram which is useful in explaining the principle based on which an ID number formed in V-shaped grooves is viewed by the optical inspecting apparatus according to the invention.
Figure 6:
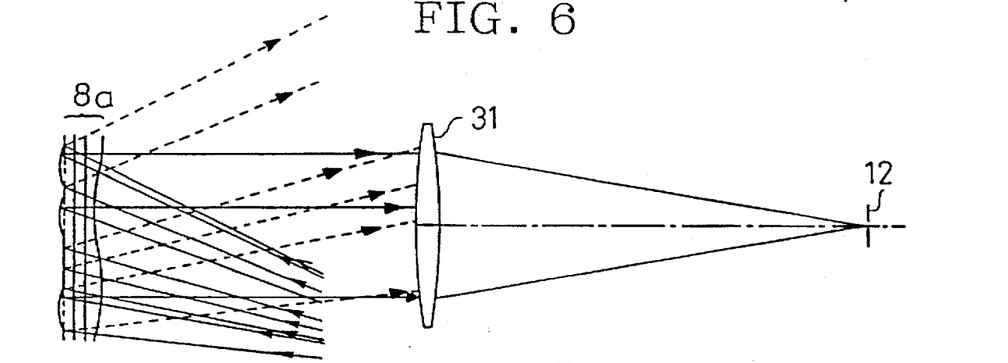
FIG. 6 is a diagram which is useful in explaining the principle based on which an ID number formed in dots of recesses is viewed in a bright pattern of an image thereof by the optical inspecting apparatus according to the invention.
Figure 7:
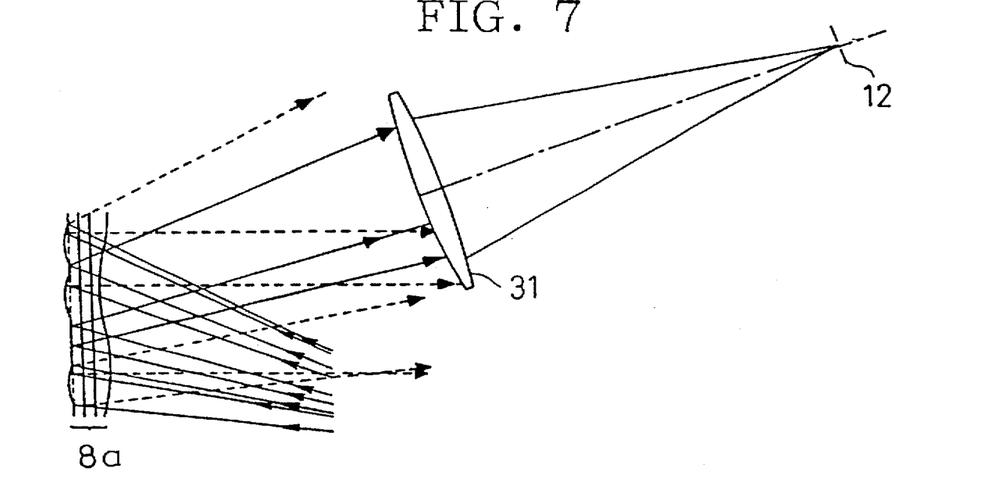
FIG. 7 is a diagram which is useful in explaining the principle based on which an ID number formed in dots is viewed in a dark pattern of an image thereof by the optical inspecting apparatus according to the invention.

Next, the method of viewing the object will be described with reference to FIG. 5 to FIG. 7 illustrating examples of the method depending on the types of the object to be inspected.

FIG. 5 shows the principle of the method of viewing an ID number formed in V-shaped grooves on the sample 8. In this case, the parallel light from the light source block 2 alone is caused to illuminate the sample surface 8a in a normal direction. Part of the parallel light is reflected from the sloping or inclined inner walls of the grooves, and transmitted in predetermined directions. Therefore, the inclining mechanism 11 is operated to incline the lens barrel 11, whereby light reflected from the ID number alone is permitted to pass into the telecentric optical system 6 while preventing the light reflected from the flat part of the sample surface 8a from entering the telecentric optical system 6. As a result, the ID number is represented by a white pattern (pattern of bright portions) of an image, while part of the sample surface 8a without the ID number is represented by a dark pattern (pattern of dark portions) of same.

FIG. 6 shows the principle of the method of viewing an ID number formed in dots of recesses (concaves) on the sample 8. The ID number is in the form of U-shaped recesses formed on the sample 8 by means of a laser beam. In this case, the lens barrel 11 is made perpendicular to the tilting stage 5, while the diffused light alone is emitted from the auxiliary light source block 4 to illuminate the sample surface 8a. The diffused light from the auxiliary light source block 4 is, as shown therein, reflected on the recesses, and part thereof is transmitted in a normal or perpendicular direction with respect to the sample surface 8a to enter the telecentric optical system 6, while the light reflected from flat part of the sample surface 8a does not enter the telecentric optical system 6. As a result, the ID number is represented by a white pattern (pattern of bright portions) of an image, while the flat part of the sample surface 8a without the ID number is represented by a dark pattern (dark positions) of same.

FIG. 7 shows the principle of the method of viewing the ID number with a pattern of bright portions and dark portions inverted from that viewed in FIG. 6. In this case, the parallel light from the light source block 2 and the diffused light from the auxiliary light source block 4 are caused to illuminate the sample surface 8a at the same time, and light reflected from the sample 8 is viewed by inclining the lens barrel 11. More specifically, the lens barrel 11 is inclined such that a portion of the parallel light (not shown in this figure) reflected from the recesses does not enter the telecentric optical system 6 (i.e. such that the recesses are represented by dark potions in the pattern of the image). As a result, almost none of light reflected from portions of the sample surface 8a formed with the ID number enters the telecentric optical system 6, thereby forming a rather dark pattern, while part of light reflected from the rest of the sample surface 8a without the ID number enters the telecentric optical system 6, thereby forming a rather bright pattern. Further, when the diffused light illuminates the sample surface 8a, a fairly large portion of the diffused light reflected from the part formed with no ID number of the sample surface Ba in predetermined diffusing angles enters the telecentric optical system 6, while light reflected from the recesses (concaves) does not enter the telecentric optical system 6. As a result, the pattern of the image formed on the recesses becomes relatively dark, whereas the image on the rest of the sample surface 8a having no recesses is relatively bright, whereby the contrast of the brightness and darkness is improved. In this connection, the image processing unit 71 automatically adjusts the light level of light emitted from the light source block 2 and the auxiliary light source block 4, to make the contrast the maximum.

Figure 8:
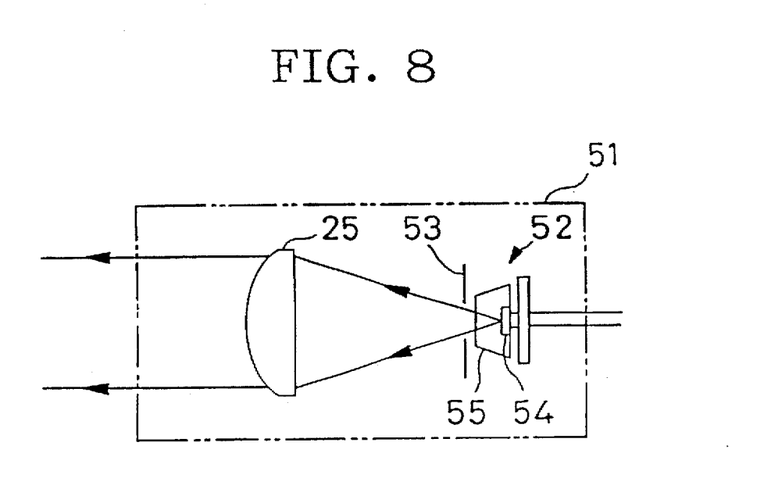
FIG. 8 is a diagram showing a variation of a light source block.

Next, variations of the light source block 2 will be described with reference to FIG. 8 and FIG. 9. In these figures, elements and component parts identical to those of referred to in the above embodiment are designated by identical reference numerals and detailed description thereof is omitted. As shown in FIG. 8, a light source block 51 in this variation is distinguished from that of the above embodiment in that an LED (light emitting diode) 52 is used in place of the halogen lamp used in the above embodiment. The light source block 51 is comprised of the LED 52, a aperture stop 53, and a collimator lens 25.

The LED 52 is formed of gallium aluminum arsenide (GaAlAs) and provides a point source of a red light having a wavelength of approximately 660 nm. The LED 52 may be of a type for emitting light having a wavelength corresponding to green or blue, and by properly selecting the LED in respect of the wavelength of light emitted therefrom depending on the reflectance and transmittance of the object to be viewed, it is possible to enhance the contrast of the image.

Further, as shown in FIG. 8, a top surface of a cover 55 formed of epoxy resin for covering a illuminant (LED chip illuminant) 54 is formed as a flat mirror-finished surface, thereby preventing light emitted from the illuminant 54 from being irregularly deflected. The LED 52 is also constructed such that the brightness of light can be adjusted by a DC current source, not shown. The LED 52 may have its cover 55 omitted, and may be constructed such that it is covered with glass which does not function as lens.

The aperture stop 53 is constructed such that the diameter of its circular opening can be continuously varied by a movable adjuster, not shown. By varying the diameter of the circular opening, an angular aperture, i.e. an area of illumination on the sample surface 8a is determined so that an image suitable for types of inspection (recognition of a symbol, check for undulation, check for a dimple, and check for a flaw) of the sample 8 is formed within the viewing block 7.

The operation of this light source block 51 will be described. The illuminant 54 of the LED 52 functions as a point source of light having no directivity due to flatness of the top of the cover 55, so that light emitted from the LED 52 forms a diverging bundle of rays. The diverging bundle of rays is passed through a aperture stop 53 which causes no optical interference, and diverges in a predetermined angular aperture to enter the collimator lens 25, where it is converted into the parallel light. The parallel light is reflected from the half mirror 3, and illuminates the sample surface 8a. In this case, the light illuminating the sample surface 8a is generated from the diverging bundle of rays, and hence produces no light source image on the sample surface 8a, which makes it unnecessary to diffusion of illuminating light by the use of a diffuser. Therefore, it is possible to enhance the efficiency of utilization of light generated from the light source. Further, the light emitted from the LED 52 has a narrow range of wavelength, which makes the wavelength-selecting filter unnecessary, as well. Therefore, the light source block 51 can have a simplified construction. Moreover, an optical fiber, which is expensive, is not used, which makes it possible to reduce manufacturing cost.

When the light source block 51 is used in the optical inspecting apparatus 1, it is desirable that the light source of the auxiliary light source block 4 is also formed of an LED, and the wavelength of light emitted therefrom agrees with that of light from the LED 52. Further, in order to make it easier to view a pattern of bright portions and dark portions of the image formed on the CCD of the viewing block 7, the wavelength-selecting filter may be employed in the light source block 51 to thereby further restrict the band of wavelength to an even smaller range.

Figure 9:
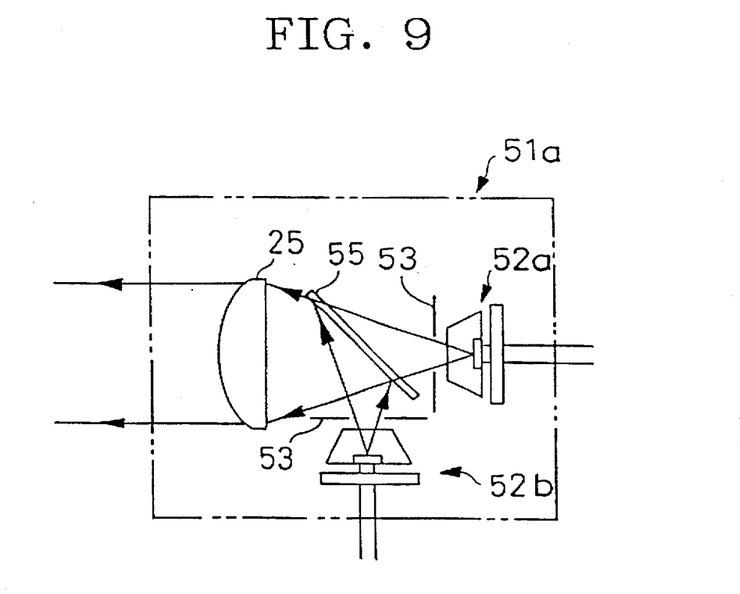
FIG. 9 is a diagram showing another variation of the light source block.

FIG. 9 shows a light source block 51a which is distinguished from that shown in FIG. 8 in that two LED's are used therein. The light source block 51a is comprised of an LED 52a arranged on an optical axis of the collimator lens 25, an LED 52b having its optical axis perpendicular to that of the collimator lens 25, and a half mirror 55 inclined through 45° with respect to the optical axis of the collimator lens 25. In this light source block 51a, the light emitted from the LED 52a passes through the half mirror 55, while light emitted from the LED 52a is reflected from the half mirror 55 to form a composite light of rays from the LED's 52a and 52b. As a result, it is possible to increase the light level when the brightness of an image is too low if a single LED is used.

The invention has been described heretofore based on preferred embodiments thereof shown only by way of example, and is by no means limited to such embodiments, but various modifications and variation can be made thereto without departing from the scope of the invention defined by claims appended hereto.

Figure 2A:
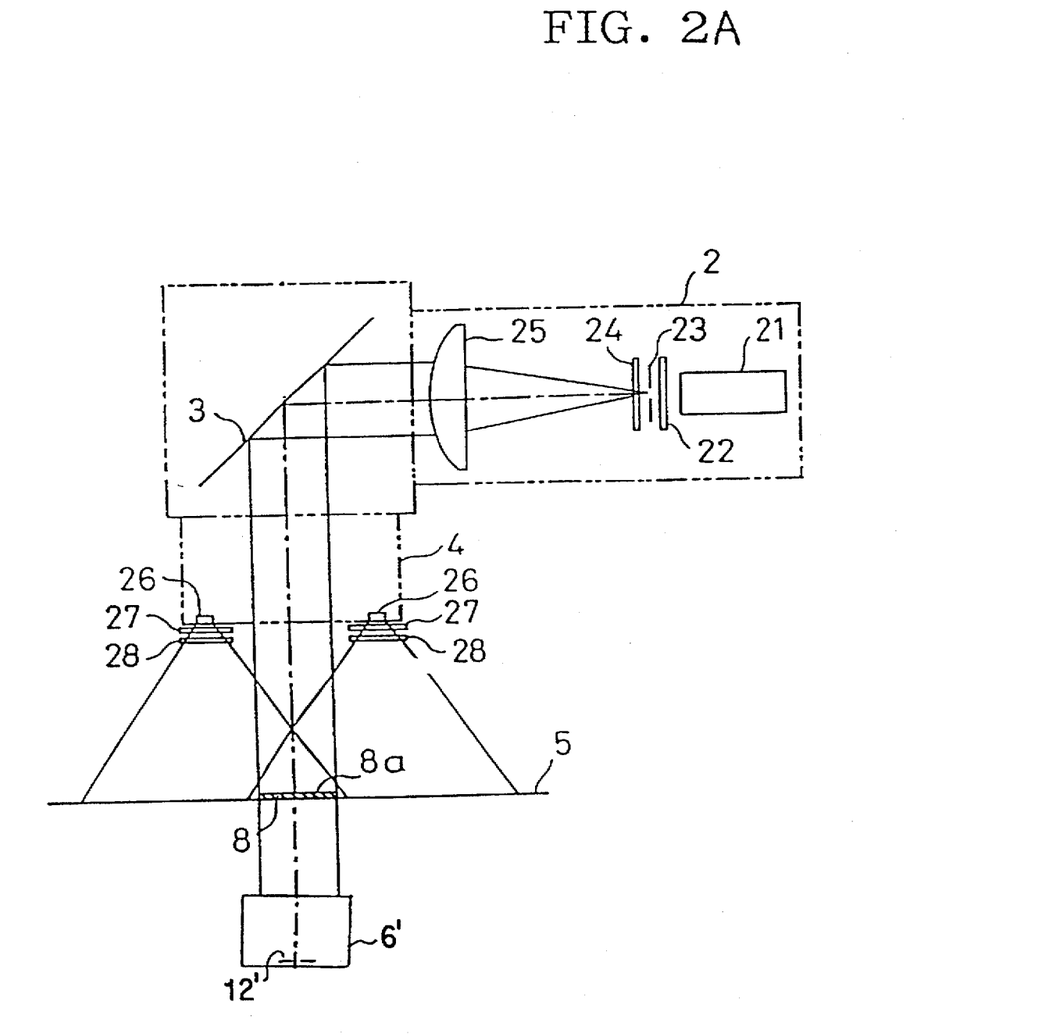

For example, although in the above embodiment, description has been made of cases where the light reflected from the sample is detected, this is not limitative, but it goes without saying that the present invention, which is characterized in that the focusing means comprises a telecentric optical system and a aperture stop arranged on a back focal plane or in its vicinity of the telecentric optical system in an image space thereof, can also be applied to an apparatus for detecting light transmitted through the sample (see FIG. 2A focusing system 12), thereby achieving the advantageous results described hereinabove, particularly, in this case, the advantageous results in detecting the state of the inside of the sample.

Further, the positional relationship between the light source block 2 or 51 and the lens barrel 11 can be inverted. That is, the apparatus may be constructed such that the light emitted from the light source 2 or 51 passes the half mirror 3, and the light reflected from the sample surface 8a is reflected from the half mirror 3 to enter the lens barrel 11.

Further, although, in the optical inspecting system of the above embodiment, description has been made of cases where the halogen lamp is used as a light emitting source (illuminant) of the light source block 2, this is not limitative, but a xenon lamp may be used as the illuminant. The type of the illuminant to be employed depends on the nature of the object (sample 8) of inspection. For example, when an object having a high reflectance, such as a semiconductor wafer, is to be inspected, either or desired one of a halogen lamp and a xenon lamp may be employed. However, when an object having a lower reflectance, such as a glass substrate, is to be inspected, it is preferable to use the xenon lamp which is capable of emitting a light having a higher luminance. Therefore, the present apparatus may be constructed such that the illuminant may be changed as desired depending on the nature of the object for inspection.

Further, the light source block 2 may be of a type having a rod glass provided on the front end of the spot fiber light guide 2.

Further, although the aperture 23 is provided in the light source block 2 for forming a point source of light, this may be replaced by a slit. In this case, the output angle (radiation angle) of the light emitted from the light source can be made wider.

Further, although, in the above embodiment, description has been made of a case where the interference filter is used as the wavelength-selecting filter 24, this is not limitative, but a colored glass filter may be used as the wavelength-selecting filter 24.

Further, although in the above embodiment, the wavelength-selecting filter 24 alone is used, an ND filter (neutral density filter) may be provided in addition to or in place of the wavelength-selecting filter. The ND filter is used for the purpose of attenuating light without changing the spectrum characteristics of the light received. The light attenuation is required e.g. in detecting an undulation of the sample surface 8a. In detecting a gentle change in the surface configuration, such as an undulation, normally-reflected components of the light are much increased, which makes the sample surface too bright, and hence the whole image formed by the reflected light becomes so bright that it is difficult to view the image, unless the illuminating light is attenuated. The light attenuation may be effected by replacement of the halogen lamp by a light source having a lower illuminance. However, the use of the ND filter facilitates the work of this adjustment.

Further, although the half mirror 3 is used in the optical inspecting system described in the above embodiment, this is not limitative, but a plate beam splitter of a wedge type may be used instead. In this case, a predetermined minute angle α is provided between two planes of the plate beam splitter. This makes it possible to cause ghost light generated by reflection at a transmitting surface of the plate beam splitter to be deviated out of a light path of desired light reflected from the reflecting surface, to thereby prevent the ghost light from being detected at the viewing block 7.

Further, although the optical inspecting apparatus uses the CCD in detecting an image, the viewing block may be constructed such that the sample surface may be viewed by way of an image formed on a screen, by camera, or by the eye. Further, in place of the CCD, there may be used any image pick-up device including a phototube, such as a photomultiplier tube.

Further, the image processing unit 71 may be adapted to perform differentiation processing, e.g. by differentiating a picture signal (original picture signal) contained in an image signal delivered from the CCD, and then adding the resulting differential signal to the original picture signal to form a new picture signal. This makes it possible to display an image in which a subtle difference in the contrast is emphasized. Further, there may be provided a brightness control circuit which makes it possible to set the brightness of an image formed by the resulting picture signal, as desired. The brightness adjustment makes it possible to easier to view the picture with brightness suitable for viewing, for example, when the state of the inside of an outline of irregularities or the outline per se is to be observed.

Further, although the iris diaphragm or the like is used as the aperture stop 12 or 53, this is not limitative, but there may be provided an aperture stop formed with a fixed circular opening, and the aperture stop is moved in the direction of the optical axis when in use.

What is claimed is:

1. An optical inspecting system comprising:
    illuminating means for illuminating a sample having an ID number-formed portion in which an ID number is formed in the form of one of grooves and dots, with a collimated light and a diffused light, said collimated light and said diffused light illuminating said sample on the same side thereof;
    focusing system, arranged separately from said illuminating means, for focusing a light from said ID number-formed portion of said sample to form an image of a brightness pattern exhibiting the ID portion of the sample,
    said focusing system comprising a telecentric optical system and an aperture stop arranged at one of a back focal plane of said telecentric optical system and in a vicinity of said telecentric optical system in an image space thereof; and
    viewing means for presenting an image of said sample based on a light passed through said focusing system.

2. An optical inspecting apparatus according to claim 1, wherein said viewing means has a light receiving block for receiving said light passed through said focusing system, and for generating and delivering an image signal, and an image processing block for performing image processing based on said image signal delivered from said light receiving block.

3. An optical inspecting apparatus according to claim 2, further comprising light level adjusting signal-generating block for generating a light level control signal for setting one of a white level voltage and a black level voltage of said image signal to a predetermined value, and a light level control block for changing the light level of said collimated light and the light level of said diffused light independently of each other, based on said light level control signal.

4. An optical inspecting system comprising:

illuminating means for illuminating a sample having an ID number-formed portion in which an ID number is formed in the form of one of grooves and dots, with a collimated light and a diffused light, said collimated light and said diffused light illuminating said sample on the same side thereof;

focusing system, arranged separately from said illuminating means, for focusing a light from said ID number-formed portion of said sample to form an image of a brightness pattern exhibiting the ID portion of the sample, a light receiving block for receiving a light passed through said focusing system, and for generating and delivering a image signal;

an image processing block for performing image processing based on said image signal delivered from said light receiving block;

light level adjusting signal-generating block for generating a light level control signal for setting one of a white level voltage and a black level voltage of said image signal to a predetermined value; and a light level control block for changing at least one of the light level of said collimated light and the light level of said diffused light independently of each other, based on said light level control signal.

5. In an apparatus for optically inspecting a condition of a sample, including:

illuminating means for illuminating the sample with collimated light;

focusing system for focusing light from the sample to form an image of a brightness pattern exhibiting the condition of the sample;

viewing means for viewing the image;

the improvement wherein said focusing system is arranged separately from said illuminating means and comprises a telecentric optical system and an aperture stop arranged at one of a back focal plane of said telecentric optical system and in a vicinity of said back focal plane of said telecentric optical system; and wherein the apparatus further comprises:

diffused light-illuminating means for illuminating the sample with diffused light on the same side thereof as said illuminating means.

6. An optical inspecting apparatus according to claim 5, wherein said focusing system includes inclination-adjusting means for inclining an optical axis thereof with respect to a light path of said light from said sample.

7. An optical inspecting apparatus according to claim 5, wherein said illuminating means comprises an LED for generating a diffused bundle of rays, as a light source.

8. An optical inspecting apparatus according to claim 5, wherein said viewing means has a light receiving block for receiving said light passed through said focusing system, and for generating and delivering an image signal, and an image processing block for performing image processing based on said image signal delivered from said light receiving block.

9. On optical inspecting apparatus according to claim 8, further comprising light level adjusting signal-generating block for generating a light level control signal for setting one of a white level voltage and a black level voltage of said image signal to a predetermined value, and a light level control block for changing the light level of said collimated light, based on said light level control signal.

10. An optical inspecting apparatus according to claim 5, wherein said focusing system focuses light reflected from the sample.

11. An optical inspecting apparatus according to claim 5, wherein said focusing system focuses light transmitted through said sample.

12. Apparatus according to claim 5, wherein light from said sample is focused only by focusing elements not commonly used by said illuminating means to illuminate said sample.

* * * * *